United States Patent [19]
Ware et al.

[11] Patent Number: 5,534,271
[45] Date of Patent: Jul. 9, 1996

[54] PROCESS FOR IMPROVING THE UTILIZATION OF FEEDSTUFFS BY RUMINANTS

[75] Inventors: Douglas R. Ware, Bothell, Wash.; Bryan E. Garner, Amarillo, Tex.

[73] Assignee: Nutrition Physiology, Amarillo, Tex.

[21] Appl. No.: 340,660

[22] Filed: Nov. 16, 1994

[51] Int. Cl.$^6$ .............................. A23K 1/18; A61K 35/74
[52] U.S. Cl. .................................. 426/2; 426/61; 426/52; 426/54
[58] Field of Search ................................... 426/2, 52, 54, 426/61

[56] References Cited

U.S. PATENT DOCUMENTS

| | | |
|---|---|---|
| 3,713,836 | 1/1973 | Carlsson . |
| 3,821,416 | 6/1974 | Thompson et al. . |
| 3,857,971 | 12/1974 | Abdo et al. . |
| 3,875,306 | 4/1975 | Alstrom ................................ 426/61 |
| 3,956,482 | 5/1976 | Hahn et al. .............................. 426/2 |
| 3,984,575 | 10/1976 | Farr . |
| 4,112,069 | 9/1978 | Huber . |
| 4,138,498 | 2/1979 | Das ........................................ 426/2 |
| 4,172,127 | 10/1979 | Huber . |
| 4,510,170 | 4/1985 | Cosentino et al. . |
| 4,518,696 | 5/1985 | Gehrman et al. . |
| 4,777,051 | 10/1988 | Nagano et al. . |
| 4,822,620 | 4/1989 | Chamberlin et al. . |
| 4,910,024 | 3/1990 | Pratt . |
| 4,943,437 | 7/1990 | Kvanta et al. . |
| 4,956,295 | 9/1990 | Sudoma . |
| 4,980,164 | 12/1990 | Manfredi et al. . |
| 5,093,121 | 3/1992 | Kuanta et al. ........................ 426/2 |
| 5,139,777 | 8/1992 | Ott et al. ........................... 424/93 A |
| 5,139,792 | 8/1992 | Ware et al. . |
| 5,256,425 | 10/1993 | Herman et al. . |

OTHER PUBLICATIONS

"*Selenomonas ruminantium*", Bergey's Manual Of Systematic Bacteriology, vol. 1, 1984, p. 652.

"*Megasphaera elsdeni*", Bergey's Manual Of Systematic Bacteriology, vol. 1, 1984, p. 685.

Scheifinger, et al. "Relationship of Lactate Dehydrogenase Specificity and Growth Rate to Lactate Metabolism by *Selenomonas ruminantium*", Applied Microbiology, Dec. 1975, pp. 916–921.

Rehberger, et al, "Identification and Application of a Propionibacteria Strain for Nitrate and Nitrate Reduction in the Rumen," OSU Cooperative Extension Service and OSU Animal Science Department present Management of High Nitrate Forages for Beef and Dairy Cattle, May 4, 1993, p. E–1.

Jensen, Mackey, *Diseases of Fedlot Cattle*, 1971, pp. 292–293.

Kunkle, Fetter & Preston, *Effect of Initial Diet On Cattle Performance and Subsequent Adaptation to high Concentrate Diets*, pp. 1263–1271 1976.

Jornal of Animal Science, vol. 66, Supplement 1, Abstracts pp. 436 and 460. (1988).

American Dairy science Association Annual Meeting and Divisional Abstracts, 1988, p. 219.

Kunkle, Fetter & Preston, *Effect of diet on in vitro and in vivo Rumen Lactate Disappearance Rate in Sheep*, 1976, pp. 1256–1262.

*Primary Examiner*—Donald E. Czaja
*Assistant Examiner*—Choon P. Koh
*Attorney, Agent, or Firm*—Novak Druce Reynolds Burt

[57] ABSTRACT

A process for improving the utilization of feedstuffs by a ruminant, the process comprising the steps of mixing a lactic acid producing bacteria culture and a lactate utilizing bacteria culture, admixing these cultures with a dry formulation or an animal feedlot diet into a composition, and administering this composition orally to ruminants. The process may be used on a continual basis to increase meat or milk production, or used during the transition from a roughage diet to a feedlot diet to prevent or minimize acidosis. The preferred embodiment utilizes *Lactobacillus acidophilus* as its lactic acid producing bacteria culture and *Propionibacterium* P-5 as its lactate utilizing bacteria culture. The composition of the process is in a dry powder form for storage at ambient temperatures for long durations.

29 Claims, No Drawings

PROCESS FOR IMPROVING THE UTILIZATION OF FEEDSTUFFS BY RUMINANTS

BACKGROUND OF THE INVENTION

1) Field of the Invention

The present invention relates generally to a process for improving the utilization of feedstuffs by ruminants, especially during the transition from a roughage diet to a feedlot diet, and more particularly to a process for administering to a ruminant a feed additive composition which includes lactic acid producing bacteria and lactic acid utilizing bacteria for improving the production from, and feed conversion efficiency of, a high grain or concentrate feedlot diet.

2) Description of the Related Art

Acute indigestion resulting from the transition from a predominantly roughage diet to a feedlot diet could be fatal to ruminants. The purpose of a feedlot operation is to fatten a ruminant, such as beef cattle, for sale or slaughter. The most common and efficient method of fattening ruminants is to feed them a high grain or high energy concentrate diet. However, this abrupt conversion from a roughage or pasture diet of plant food, mainly cellulose, to a feedlot diet predominantly composed of grains and starches can cause decreased production to feedlot cattle and even death from acidosis. Similar diet transitions can result in a decrease in milk production for dairy cows as well as death.

As discussed in *Diseases of Feedlot Cattle*, Second Edition, Lea & Febiger, p 292–293 (1971), acute indigestion in cattle is caused by sudden consumption of large amounts of grain, green corn, green apples or other easily fermentable feeds. During a roughage diet, cellulosic bacteria predominates in ruminal microflora. Volatile fatty acids are usually formed in the following proportions: acetic, 67%; propionic, 19%; and butyric, 14%. These acids constitute an important nutrient from cellulose digestion. However, during the fattening process at the feedlot, cattle are placed on a high grain diet. On a high grain diet, the ruminal microflora ferment the new feed and produce 100 or more milli-moles per liter of lactic acid resulting in the rumen becoming immobilized. A large portion of the lactic acid accumulated may be the D(−) isomer which is an unavailable energy source for the ruminant and thus builds up in the rumen. Absorption of the acid into the blood lowers the blood pH and diminishes the content of bicarbonate and glucose bringing about acidosis. Compensation for the acidic condition occurs by excretion of carbonic acid through rapid respiration and by excretion of hydrogen ions through urine. Affected cattle may survive through compensation, however, severe acidosis is fatal. Additionally, the increase in acidity of the rumen damages the mucosa which may result in necrosis of the epithelium which enables bacteria such as Spherophorus necrophorus to enter the veins and be conveyed to the liver where liver abscesses may form in surviving animals.

Lactic acid and products containing lactic acid have been found to enhance gains in the starting period of cattle (first 28 days) and reduce liver abscesses when given prior to the transition from a roughage diet to a feedlot diet. Various strains of *Lactobacillus acidophilus* have been isolated which restore and stabilize the internal microbial balance of animals. Manfredi et al, U.S. Pat. No. 4,980,164, is such a strain of *Lactobacillus acidophilus* which has been isolated for enhancing feed conversion efficiency. The *Lactobacillus acidophilus* strain of the Manfredi et al patent has been designated strain BT1386 and received accession number ATCC No. 53545 from the American Type Culture Collection in Rockville, Md. Strain ATCC 53545 demonstrates a greater propensity to adhere to the epithelial cells of some animals which would increase the bacteria cultures' ability to survive, initiate and maintain a population within an animal intestine. Thus, the primary mode of action as previously understood relative to *Lactobacillus acidophilus* occurs post-ruminally.

Another strain of *Lactobacillus acidophilus* isolated for restoring and stabilizing the internal microbial balance of animals is disclosed in Herman et al, U.S. Pat. No. 5,256, 425. The *Lactobacillus acidophilus* strain of the Herman et al patent has been designated strain BT1389 and received accession number ATCC No. 55221 from the American Type Culture Collection in Rockville, Md. Strain ATCC 55221 is a further improvement on strain ATCC 53545 in that it is easily identified and quantified due to its resistance to antibiotics such as erythromycin and streptomycin.

The above-mentioned strains of *Lactobacillus acidophilus* are perfectly good lactic acid producing organisms. However, more than a lactic acid producing organism is needed to improve the utilization of feedstuffs by ruminants, especially during the transition from a roughage diet to a feedlot diet. The problem with the increase of D-lactate in the rumen must also be resolved in order to facilitate the transition of ruminants from a roughage diet to a feedlot diet.

Administration of bacteria to cattle is also problem due to the extreme sensitivity of organisms like *Lactobacillus acidophilus* which are difficult to maintain in a viable state at ambient temperatures. Also, lactic acid is corrosive to feedlot and feedmill equipment and metallic components The present invention relates to a novel process which addresses the problems associated with the utilization of feedstuffs by ruminants which have been set forth above, especially the problems associated with the transition from a roughage diet to a feedlot diet.

SUMMARY OF THE INVENTION

The present invention is a novel process for improving the utilization of feedstuffs by ruminants, especially during the transition from a roughage diet to a feedlot diet. The novel process facilitates the uptake and utilization of lactate by a ruminant, preparing the ruminant for the high levels of lactic acid associated with a high grain diet. The process comprises mixing a lactic acid producing bacteria culture and a lactate utilizing bacteria culture, admixing these cultures with a ruminant feedlot diet essentially consisting of corn, dried grain, alfalfa, and corn meal to form a composition, and administering this composition orally to the ruminants. The lactic acid producing bacteria could include, but is not limited to, the following: *Lactobacillus acidophilus; Lactobacillus plantarum; Streptococcuus faecium; Lactobacillus casei; Lactobacillus lactis; Lactobacillus enterii; Lactobacillus fermentum; Lactobacillus delbruckii; Lactobacillus helveticus; Lactobacillus curvatus; Lactobacillus brevis; Lactobacillus bulgaricus; Lactobacillus cellobiosuus; Streptococcus lactis; Streptococcus thermophilus; Streptococcus cremoris; Streptococcus diacetylactis; Streptococcus intermedius; Bifidobacterium animalis; Bifidobacterium adolescentis; Bifidobacterium bifidum; Bifidobacterium infantis; Bifidobacterium longum; Bifidobacterium thermephilum; Pediococcus acidilactici;* and, *Pediococcus pentosaceus*. The lactate utilizing bacteria could include, but is not limited to, the following: Propionibacterium, *Propionibacterium freudenreichii, Propionibacterium shermanii,*

*Propionibacterium acidi-propionici, Propionibacterium globosum, Propionibacteriuum jensenii, Peptostreptococcus asaccharolyticus, Negasphaera elsdenii* and *Selenomonas ruminantium.*

In the preferred embodiment, the lactate producing bacteria is the strain of *Lactobacillus acidophilus* designated as *Lactobacillus acidophilus* ATCC 53545. Also in the preferred embodiment, the lactate utilizing bacteria is the strain of Propionibacterium designated as Propionibacterium P-5. However, other strains of Propionibacterium may be used such as Propionibacterium P-99 and Propionibacterium P-42.

In one embodiment, the novel process is designed for continual administration to ruminants throughout the feeding period in order to improve the production of meat or milk from the ruminants, through adjusting the microbial content of the rumen of the ruminants. In this embodiment, the process comprises mixing a lactic acid producing bacteria culture and a lactate utilizing bacteria culture, admixing these cultures with a dry formulation of growth substrates, enzymes, sugars, carbohydrates, extracts and growth promoting micro-ingredients, into a composition, and administering the composition orally to the ruminants. The lactic acid producing bacteria culture produces lactic acid in the rumen in order to promote the growth of the lactate utilizing bacteria culture in order to prepare the rumen for a feed diet which generates high levels of lactic acid. The lactic acid in the rumen is then consumed by the lactate utilizing bacteria which in turn promotes ruminant production. In this embodiment, an animal feedlot diet consisting of corn, dried grain, alfalfa, and corn meal may be substituted for the dry formulation.

In another embodiment, the novel process is designed for improving the transition of ruminants from a roughage diet to a feedlot diet through adjusting the microbial content of the rumen of the ruminants. In this embodiment, the process comprises mixing a lactic acid producing bacteria culture and a lactate utilizing bacteria culture, admixing these cultures with a dry formulation of growth substrates, enzymes, sugars, carbohydrates, extracts and growth promoting micro-ingredients into a composition, and then administering this composition orally to the ruminants. The lactic acid producing bacteria culture produces lactic acid in the rumen in order to promote the growth of the lactate utilizing bacteria culture in order to prepare the rumen for a feed diet which generates high levels of lactic acid. The lactic acid in the rumen is then consumed by the lactate utilizing bacteria limiting acidosis in the ruminant. In this embodiment, an animal feedlot diet consisting of corn, dried grain, alfalfa, and corn meal may be substituted for the dry formulation.

If used on a continual basis for dairy cows, the novel process will increase milk production. If used for beef cattle, the novel process will increase meat production. When used on a continual basis for increasing production, $10^8$ to $10^{10}$ colony forming units (CFU)/day should be fed to the ruminants. When used to improve the transition from a roughage diet to a feedlot diet, much higher levels of the bacteria cultures must be used, approximately $10^{11}$ to $10^{12}$ CFU/day. The novel process applies the composition in a dry powder form which enables the sensitive bacteria to survive at ambient temperatures. Ruminants such as feedlot cattle and dairy cows are the preferred ruminants for application of the novel process.

It is the primary object of the present invention to provide a novel process which will improve the utilization of feedstuffs by ruminants.

It is a further object of the present invention to provide a process which will facilitate the transition from a roughage diet to a feedlot diet for a ruminant.

It is a further object of the present invention to provide a process which will be used on a continual basis to improve production from the ruminant.

It is a further object of the present invention to provide a process which will facilitate the uptake and utilization of D-lactate in the rumen during the transition from a roughage diet to a feedlot diet for a ruminant.

It is a further object of the present invention to provide a process which will increase milk production in dairy cows.

Other objects and advantages will become apparent from a reading of the detailed description and the appended claims.

DETAILED DESCRIPTION OF THE INVENTION

The present invention is a novel process for improving the utilization of feedstuffs by ruminants such as cattle and sheep. The novel process counters the effects of acidosis brought about by a transition from a roughage diet to a high grain diet which occurs when cattle are brought to a feedlot for fattening. The novel process may also be utilized as a continual feed product for the production phase of the ruminant in order to counter any gyrations in the ruminants intake pattern.

The novel process encourages the premature growth of lactate producing bacteria in the rumen in order to feed and promote the growth of lactate utilizing bacteria in the rumen. By supplying a mixture of a lactate producing bacteria and a lactate utilizing bacteria, the novel process provides the ruminant with the capability to more quickly adapt to a high grain or high starch diet which results in qualitative changes in the ruminal microflora where fermentation of the high grain feed produces high levels of lactic acid. By providing the ruminant with a means for utilizing the lactic acid, the novel process decreases lactic acid indigestion and possible liver damage.

The bacteria cultures of the novel process are admixed with a dry formulation of additives including but not limited to growth substrates, enzymes, sugars, carbohydrates, extracts and growth promoting micro-ingredients. The sugars could include the following: lactose; maltose; dextrose; malto-dextrin; glucose; fructose; mannose; tagatose; sorbose; raffinose; and galactose. The sugars range from 50–95%, either individually or in combination. The extracts could include yeast or dried yeast fermentation solubles ranging from 5–50%. The growth substrates could include: trypticase, ranging from 5–25%; sodium lactate, ranging from 5–30%; and, Tween 80, ranging from 1–5%. The carbohydrates could include mannitol, sorbitol, adonitol and arabitol. The carbohydrates range from 5–50% individually or in combination. The micro-ingredients could include the following: calcium carbonate, ranging from 0.5–5.0%; calcium chloride, ranging from 0.5–5.0%; dipotassium phosphate, ranging from 0.5–5.0%; calcium phosphate, ranging from 0.5–5.0%; manganese proteinate, ranging from 0.25–1.00%; and, manganese, ranging from 0.25–1.00%.

In another embodiment, the bacteria cultures of the novel process are admixed with an animal feedlot diet consisting of corn, dried grain, alfalfa, and corn meal. With either embodiment, $10^8$ to $10^{10}$ CFU/day should be fed to the ruminants on a continual basis to increase production while $10^{11}$ to $10^{12}$ CFU/day should be fed to the ruminants to improve the transition from a roughage diet to a feedlot diet.

As has been shown in experiments, the novel process will initially increase the total lactate content in the rumen. Then, an accelerated decrease in total lactate takes place as the lactate utilizing bacteria begin to consume the lactate. The lactate is converted into acetate and propionate, as well as other volatile fatty acids, which will be used to synthesize glucose in the liver, the ultimate end product and major energy source for the ruminants. The novel process also tends to reduce the acetate/propionate ratio in ruminants which results in increased energy conversion efficiency.

The novel process also stabilizes the rumen pH of ruminants administered the novel composition which demonstrates a likelihood of limiting acidosis in the ruminants.

The present invention will be described in the following examples which will demonstrate the efficacy of the novel process, however, the scope of the present invention is not to be limited by these examples.

EXAMPLE I

Holstein cows from one of the highest producing commercial herds in Washington and certainly in the nation were used in a field study of the process of the present invention. Each trial used the same set of nine-hundred fifty cows which were placed on a first diet as a control and then switched to a treated diet, thus the same set of nine-hundred fifty cows were their own control group. The milk production of the cows on each trial was measured as an average of the daily production for all cows on a daily basis. In the first trial, the group of nine-hundred fifty cows were given a basic diet consisting of steam flaked corn, barley, alfalfa, corn silage and protein supplements for twenty-five days. The same group of nine-hundred fifty cows were then given the same basic diet along with a dosage of $4\times10^8$ cfu per head daily of *Lactobacillus acidophilus* ATCC 53545 for sixty-five days. As is set forth in Table I, the cows in the first trial had an increase in their average daily milk production of 1.27 kilograms when given the treated diet.

TABLE I

| Performance data of Lactating Dairy Cows | | | |
|---|---|---|---|
| | Control | Treated with L. Acidophilus | Difference |
| Days | 25 | 65 | |
| Avg. Daily milk production | 35.59 Kg | 36.86 Kg | +1,27 Kg |

In the second trial, the nine-hundred fifty cows were given the same basic diet from the first trial along with a dosage of $4\times10^8$ cfu per head daily of *Lactobacillus acidophilus* ATCC 53545 for twenty-five days. The same group of nine-hundred fifty cows were then given the basic diet along with a dosage of $4\times10^8$ cfu per head daily of *Lactobacillus acidophilus* ATCC 53545 and $4\times10^9$ cfu per head daily of a fifty-fifty mixture Propionibacterium P-5 and Propionibacterium P-99 for thirty-six days. As is set forth in Table II, the cows in the second trial had an increase of 1.27 kilograms in the average daily milk production when given the basic diet treated with *Lactobacillus acidophilus* ATCC 53545 and a fifty-fifty mixture of Propionibacterium P-5 and Propionibacterium P-99 over the basic diet treated with only *Lactobacillus acidophilus* ATCC 53545.

TABLE II

| Performance Data of Lactating Dairy Cows | | | |
|---|---|---|---|
| | Control treated with L. Acidophilus | Treated with L. Acidophilus and Propionibacterium | Difference |
| Days | 25 | 36 | |
| Avg. Daily milk production | 40.32 Kg | 41.59 Kg | +1.27 Kg |

In the third trial, the group of nine-hundred fifty cows were given the basic diet of the first trial along with a dosage of $4\times10^8$ cfu per head daily of *Lactobacillus acidophilus* ATCC 53545 for fifty-six days. The same group of nine-hundred fifty cows were then given the basic diet along with a dosage of $4\times10^8$ cfu per head daily of *Lactobacillus acidophilus* ATCC 53545 and $4\times10^9$ cfu per head daily of a fifty-fifty mixture Propionibacterium and Propionibacterium P-99 for sixty-six days. As is set forth in Table III, the cows in the third trial had an increase of 2.95 kilograms in the average daily milk production when given the basic diet treated with *Lactobacillus acidophilus* ATCC 53545 and a fifty-fifty mixture of Propionibacterium P-5 and Propionibacterium P-99 over the basic diet treated with only *Lactobacillus acidophilus* ATCC 53545.

TABLE III

| Performance Data of Lactating Dairy Cows | | | |
|---|---|---|---|
| | Control treated with L. Acidophilus | Treated with L. Acidophilus and Propionibacterium | Difference |
| Days | 56 | 66 | |
| Avg. Daily milk production | 39.13 Kg | 42.09 Kg | +2.95 Kg |

As is shown by Tables I, II, and III, lactating dairy cows exhibited a marked increase in the amount of average daily milk production when given the composition of *Lactobacillus acidophilus* ATCC 53545, Propionibacterium P-5 and Propionibacterium P-99 along with the cows basic diet. The composition was applied through an Accurate delivery system which rehydrates the freeze dried product on a batch to batch basis. The freeze dried powder was augered from a polyvinyl hopper which delivered 0.25 grams of powder per head into a flushing system which dilutes the powder and sprays it on the feed to be mixed.

EXAMPLE II

A feedlot study conducted at the University of Nebraska studied the metabolism of five European crossbred steers which were placed on an all concentrate diet to induce subclinical acidosis. All the cattle were adapted to a fifty percent concentrate diet for fourteen days and then an one-hundred percent concentrate diet for twenty-four hours. The concentrate consisted of equal parts of finely ground dry corn and dry rolled wheat. All of the cattle were on the same basic diet with only the microbial treatment being different from set to set. A first set of steers were given a daily dosage of $1\times10^8$ CFU/day of *Lactobacillus acidophilus* ATCC 53545 alone, and a second set of steers were given a daily dosage of $1\times10^8$ CFU/day of *Lactobacillus acidophilus* ATCC 53545 in combination with a daily dosage of $1\times10^{10}$ CFU/day of Propionibacterium P-5. A third set of steers were a control group which were given only the concentrate diet. The powder composition was mixed with water and applied via a hand applicator directly to the feed of the steers. Certain metabolic parameters were measured to determine the effectiveness of the strains of bacteria alone and in combination. These metabolic parameters were measured at the beginning of the concentrate diet, hour zero, at hour nine postfeeding, at hour twelve postfeeding, at hour fifteen postfeeding, and at hour eighteen postfeeding. The metabolic parameters measured were: total organic acids; D-lactate content; L-lactate content; total lactate content; acetate content; and propionate content. Table IV shows the total organic acid content of the three groups of steers.

TABLE IV

Measure of Total Organic Acids in
Steers with Induced Subclinical Acidosis

| Hours | Control | Treated with L. Acidophilus | Treated with L. Acidophilus and Propionibacterium |
|---|---|---|---|
| | | in mmol/100 ml | |
| 0 | 140.0 | 134.4 | 128.5 |
| 9 | 308.5 | 400.4 | 634.2 |
| 12 | 427.4 | 669.6 | 1054.0 |
| 15 | 735.2 | 697.3 | 1258.3 |
| 18 | 764.8 | 362.0 | 443.4 |

The change from hour fifteen postfeeding through hour eighteen postfeeding in millimoles per 100 milliliters, and the percent change are illustrated in Table V. Steers treated with *Lactobacillus acidophilus* ATCC 53545 in combination with Propionibacterium P-5 showed almost a sixty five percent decrease in the amount of organic acids in their rumen as compared to a forty-eight percent decrease for those steers treated with only *Lactobacillus acidophilus* ATCC 53545, and a four percent increase in the control steers. The decrease in total organic acids for the treated steers demonstrated increased microbial activity in the steers' rumens which provides more substrate for the steers to convert into microbial protein beneficial for protein synthesis which in turn increases the growth rate of the steer.

TABLE V

Measure of Total Organic Acids in
Steers with Induced Subclinical-Acidosis
Change From Hour 15 Through Hour 18

| | Control | Treated with L. Acidophilus | Treated with L. Acidophilus and Propionibacterium |
|---|---|---|---|
| mmol/100 ml | 29.6 | (335.3) | (814.9) |
| Percent | 4.0 | (48.1) | (64.8) |

Table VI shows the D-lactate content, L-lactate content and total lactate content in millimoles per 100 milliliters of rumen fluid for the control steers.

TABLE VI

Measure of Lactate in Steers with Induced Subclinical Acidosis
Control Steers

| Hour | D-Lactate | L-Lactate | Total Lactate |
|---|---|---|---|
| | in mmol/100 ml | | |
| 0 | 3.5 | 2.9 | 6.4 |
| 9 | 45.1 | 88.4 | 133.5 |
| 12 | 137.2 | 206.4 | 343.6 |
| 15 | 296.9 | 279.8 | 576.7 |
| 18 | 286.6 | 231.7 | 518.3 |

Table VII shows the D-lactate content, L-lactate content and total lactate content in millimoles per 100 milliliters of rumen fluid for the steers treated with *Lactobacillus acidophilus* ATCC 53545.

TABLE VII

Measure of Lactate in Steers with Induced Subclinical Acidosis
Steers Treated with L. Acidophilus

| Hour | D-Lactate | L-Lactate | Total Lactate |
|---|---|---|---|
| | in mmol/100 ml | | |
| 0 | 3.3 | 2.1 | 5.4 |
| 9 | 79.7 | 155.6 | 235.3 |
| 12 | 284.6 | 432.8 | 717.4 |
| 13 | 420.6 | 147.3 | 567.9 |
| 18 | 209.7 | 36.6 | 246.3 |

Table VIII shows the D-lactate content, L-lactate content and total lactate content in millimoles per 100 milliliters of rumen fluid for the steers treated with *Lactobacillus acidophilus* ATCC 53545 in combination with Propionibacterium P-5.

TABLE VIII

Measure of Lactate in Steers with Induced Subclinical Acidosis
Steers Treated with L. Acidophilus and Propionibacterium

| Hour | D-Lactate | L-Lactate | Total Lactate |
|---|---|---|---|
| | in mol/100 ml | | |
| 0 | 3.1 | 1.8 | 4.9 |
| 9 | 197.2 | 260.6 | 457.8 |
| 12 | 428.8 | 475.7 | 904.5 |
| 15 | 660.8 | 423.3 | 1084.1 |
| 18 | 209.3 | 142.6 | 351.9 |

The change of lactate content in all the steers from hour fifteen postfeeding through hour eighteen postfeeding in millimoles per 100 milliliters, and the percent change are illustrated in Table IX. Steers treated with *Lactobacillus acidophilus* ATCC 53545 in combination with Propionibacterium P-5 showed more than a sixty-seven percent decrease in the amount of lactate in their rumen as compared to a fifty-six percent decrease for those steers treated with only *Lactobacillus acidophilus* ATCC 53545, and a ten percent decrease in the control steers. Table VII shows that the steers treated with *Lactobacillus acidophilus* ATCC 53545 had a moderate increase in lactate levels up to hour fifteen postfeeding whereafter the lactate levels dropped quickly by hour eighteen postfeeding. Table VIII shows that steers treated with *Lactobacillus acidophilus* ATCC 53545 in combination with Propionibacterium P-5 had a dramatic increase in lactate levels up to hour fifteen postfeeding whereafter the lactate levels dropped below the control steers levels by hour eighteen postfeeding. The dramatic decrease in total lactate for the treated steers demonstrated increased microbial activity in the steers' rumens which provides more substrate for the steers to convert into microbial protein beneficial for protein synthesis which in turn increases the growth rate of the steer. Increased total organic acids and total lactate represent increased microbial activity because these major metabolic intermediates represent the conversion of starch into lactate then to acetate, propionate and other volatile fatty acids (VFA) of lesser importance such as butyrate, valerate, isobutyrate and isovalerate. These major metabolic intermediates are then used to synthesize microbial protein in the rumen, or are absorbed through the rumen wall, transported to the liver where they are converted into glucose which is ultimately the major six carbon end product which can be utilized as energy by the ruminant.

Gas and Liquid chromatography was used to analyze the VFA content of the deproteinized rumen fluid to obtain the measurements for the acetate and propionate shown on Tables X–XIII. The D and L Lactate measurements were obtained through a spectrophotometric assay.

TABLE IX

Measure of Lactate in Steers Induced with Subclinical Acidosis
Change From Hour 15 Through Hour 18

|  | Control | Treated with L. Acidophilus | Treated with L. Acidophilus and Propionibacterium |
|---|---|---|---|
| mol/100 ml | (58.4) | (321.6) | (732.2) |
| Percent | (10.1) | (56.6) | (67.5) |

Table X shows the acetate content and propionate content in millimoles per 100 milliliters, and the acetate/propionate ratio of the control steers.

TABLE X

Acetate and Propionate Content
in a Rumensin ™ Containing Diet
Control Steers

| Hour | Acetate | Propionate | Acetate/Propionate Ratio |
|---|---|---|---|
|  | in mmol/100 ml | | |
| 0 | 98 | 22 | 4.4 |
| 9 | 111 | 41 | 2.7 |
| 12 | 114 | 47 | 2.4 |
| 18 | 99 | 40 | 2.5 |
| 18 | 74 | 34 | 2.2 |

Table XI shows the acetate content and propionate content in millimoles per 100 milliliters, and the acetate/propionate ratio of the steers treated with *Lactobacillus acidophilus* ATCC 53545.

TABLE XI

Acetate and Propionate Content
in a Rumensin ™ Containing Diet
Steers Treated with L. Acidophilus

| Hour | Acetate | Propionate | Acetate/Propionate Ratio |
|---|---|---|---|
|  | in mmol/100 ml | | |
| 0 | 93 | 20 | 4.7 |
| 9 | 93 | 41 | 2.3 |
| 12 | 64 | 30 | 2.1 |
| 15 | 74 | 33 | 2.2 |
| 18 | 58 | 34 | 1.7 |

Table XII shows the acetate content and propionate content in millimoles per 100 milliliters, and the acetate/propionate ratio of the steers treated with *Lactobacillus acidophilus* ATCC 53545 in combination with Propionibacterium P-5.

TABLE XII

Acetate and Propionate Content
in a Rumensin ™ Containing Diet
Steers Treated with L. Acidophilus and Propionibacterium

| Hour | Acetate | Propionate | Acetate/Propionate Ratio |
|---|---|---|---|
|  | in mmol/100 ml | | |
| 0 | 86 | 23 | 3.7 |
| 9 | 118 | 35 | 3.4 |
| 12 | 78 | 43 | 1.8 |
| 15 | 104 | 44 | 2.4 |
| 18 | 43 | 33 | 1.3 |

The percent change in the acetate/propionate ratio from hour fifteen postfeeding through hour eighteen postfeeding in all three sets of steers is illustrated in Table XIII. Steers treated with *Lactobacillus acidophilus* ATCC 53545 in combination with Propionibacterium P-5 showed more than an eighty-four percent decrease in the ratio of acetate to propionate in their rumen as compared to a twenty-two percent decrease for those steers treated with only *Lactobacillus acidophilus* ATCC 53545, and a twelve percent decrease in the control steers. The dramatic reduction in the acetate/propionate ratio for the steers treated with *Lactobacillus acidophilus* ATCC 53545 in combination with Propionibacterium P-5 is surprising, especially in a diet already containing Rumensin which has the proposed mode of action of favoring propionate production and reducing the acetate/propionate ratio. The relative energy conversion efficiency is sixty-two percent for acetate and one-hundred nine percent for propionate. Thus, a lower acetate/propionate ratio is favorable for increased animal production since the desired end product is the six carbon sugar molecule glucose which is synthesized by the liver, and the most efficient pathway for glucose synthesis is through the synthesis of two three carbon propionic acid molecules into the six carbon glucose molecule. This reaction occurs without a net energy loss. However, the acetate conversion is less efficient since it is the primary precursor for fat synthesis. To be utilized as sugar, this fat must then be broken down to be converted to glucose which results in a net energy cost, making this pathway a less energetically efficient conversion than the direct conversion of propionate to glucose.

TABLE XIII

Measure of Acetate/Propionate in
Steers Induced with Subclinical Acidosis
Percent Change From Hour 15 Through Hour 18

|  | Control | Treated with L. Acidophilus | Treated with L. Acidophilus and Propionibacterium |
|---|---|---|---|
| Percent | (12) | (22.7.) | (84.6) |

EXAMPLE III

A study involving three-hundred Holstein feedlot steers, each steer weighing approximately two-hundred twenty-seven kilograms, was conducted in the Texas Panhandle. The study involved taking fecal pH measurements from the steers to determine the effects of the novel process of the present invention on the steers' rumen. The steers fecal pH was measured prior to administration, at ten days with application of the process to the steer's feed, and at twenty-three days with application of the process to the steer's feed. The steers were given a total colony forming units (CFU) count of $10^8$ organisms per head per day containing *Lactobacillus acidophilus* strain ATCC 53545 and Propionibacterium P5. As is demonstrated in Table XIV, the pH measurements clearly indicate a definite increase in the fecal pH as the steers underwent the process on a daily basis. Thus, there was less acidity in the steer's digestive tract as a result of the process. The composition of the process was applied using a volumetric metering device with a storage bin that allows several hours or days of storage of the composition in a dry powder form. The composition, in a dry powder form, is discharged into a water or aqueous bath just prior to being sprayed onto the feed. This eliminates any temperature control or two step mixing process for application.

TABLE XIV

Measure of Fecal pH of Steers Treated with
*L. Acidophilus* and *Propionibacterium*

|  | Zero Days | Ten Days | Twenty-three Days |
|---|---|---|---|
| Mean pH | 5.65 | 6.12 | 6.18 |
| Std, Dev. = +/– | 0.34 | 0.40 | 0.48 |
| Coef. of Var., % = +/– | 6.08 | 6.53 | 7.79 |

EXAMPLE IV

The lactic acid producer *Lactobacillus Acidophilus* is a very sensitive organism that is difficult to maintain in a viable state at ambient temperatures. Two studies were conducted at the Silliker Laboratories in Chicago, Ill., an FDA approved laboratory, to demonstrate the stability of the lactic acid producer *Lactobacillus Acidophilus,* and its capability to survive on feed that is being fed to steers. The first study measured the levels of Lactic acid bacteria on feedlot ration during storage at twenty-one degrees Celsius, and at thirty-five degrees Celsius. *Lactobacillus Acidophilus* strain LA45 was used in both studies. Table XV demonstrates that the levels of Lactic acid bacteria eventually increased within the twenty-four hour period when the temperature was maintained at a constant twenty-one degrees Celsius. The control count represents Aerobic mesophilic bacteria. The amount of anaerobic Lactic acid bacteria counts in LA45 is approximately $8.7 \times 10^9$.

TABLE XV

Levels of Lactic acid Bacteria on Feed
During Storage at Twenty-One Degrees Celsius

| Hour | Control | LA45 (500 g) | LA45 (50 g) | LA45 (5 g) |
|---|---|---|---|---|
|  |  | CFU/gram |  |  |
| 0 | $6.3 \times 10^5$ | $4.3 \times 10^9$ | $4.3 \times 10^8$ | $4.3 \times 10^7$ |
| 4 | $4.9 \times 10^5$ | $2.2 \times 10^9$ | $1.4 \times 10^8$ | $2.7 \times 10^7$ |
| 8 | $2.5 \times 10^6$ | $4.7 \times 10^9$ | $1.7 \times 10^9$ | $2.6 \times 10^8$ |
| 24 | $2.0 \times 10^8$ | $1.9 \times 10^{10}$ | $1.7 \times 10^9$ | $9.0 \times 10^8$ |

Table XVI demonstrates the ability of *Lactobacillus Acidophilus* strain LA45 to maintain viability on a feedlot ration during storage at a constant temperature of thirty-five degrees Celsius. As in Table XV, the Lactic acid bacteria levels eventually increased within the twenty-four hour period.

TABLE XVI

Levels of Lactic acid Bacteria on Feed
During Storage at Thirty-Five Degrees Celsius

| Hour | Control | LA45 (500 g) | LA45 (50 g) | LA45 (5g) |
|---|---|---|---|---|
|  |  | CFU/gram |  |  |
| 0 | $6.3 \times 10^5$ | $4.3 \times 10^9$ | $4.3 \times 10^8$ | $4.3 \times 10^7$ |
| 4 | $2.7 \times 10^4$ | $1.8 \times 10^3$ | $2.7 \times 10^8$ | $3.7 \times 10^7$ |
| 8 | $4.6 \times 10^6$ | $2.6 \times 10^9$ | $1.3 \times 10^9$ | $2.6 \times 10^8$ |
| 24 | $2.5 \times 10^8$ | $1.3 \times 10^{10}$ | $3.5 \times 10^9$ | $2.2 \times 10^9$ |

The second study to demonstrate the viability of *Lactobacillus Acidophilus* involved subjecting the bacteria to various high temperatures over a five day period. The bacteria was sampled at twenty-four intervals over the five day period from open containers stored in incubators at a constant temperatures of twenty-four degrees Celsius, thirty-two degrees Celsius, forty degrees Celsius, and forty-nine degrees Celsius. *Lactobacillus Acidophilus* strain LA45 was used in the study. Table XVII demonstrates the results of this study. As is shown in Table XVII, there were non-appreciable changes in the counts over the five day period except at the highest temperature of forty-nine degrees Celsius. At the highest temperature, there was an appreciable decrease in the bacteria count of the *Lactobacillus Acidophilus* strain LA45. However, mean daily average temperatures in all feedlot conditions in the United States do not average above thirty-five degrees Celsius. Normal use conditions of *Lactobacillus Acidophilus* strain LA45 dictates that the product would be in the machine less than forty-eight hours.

TABLE XVII

Stability of *Lactobacillus acidophilus* Strain LA 45 at
Various High Temperature Levels
Over a Five Day Period of Time

| Hour | 24 degrees C. | 32 Degrees C. | 40 Degrees C. | 49 Degrees C. |
|---|---|---|---|---|
|  |  | CFU/gram |  |  |
| 0 | $3 \times 10^9$ | $3 \times 10^9$ | $3 \times 10^9$ | $2 \times 10^9$ |
| 24 | $5 \times 10^9$ | $1 \times 10^9$ | $2 \times 10^9$ | $3 \times 10^8$ |
| 48 | $3 \times 10^{10}$ | $2 \times 10^9$ | $3 \times 10^9$ | $1 \times 10^8$ |
| 72 | $8 \times 10^8$ | $6 \times 10^9$ | $5 \times 10^6$ | $2 \times 10^8$ |
| 96 | $5 \times 10^9$ | $3 \times 10^8$ | $2 \times 10^9$ | $35 \times 10^6$ |
| Average | $9 \times 10^9$ | $2 \times 10^9$ | $2 \times 10^9$ | $5 \times 10^8$ |

While the preferred embodiment of the invention has been shown and described, it will be apparent to those skilled in this art that various modifications may be made in the embodiment without departing from the spirit of the present invention. Therefore, the embodiments of the invention in which an exclusive property or privilege is claimed are defined as follows:

1. A process for improving the utilization of feedstuffs by ruminants through adjusting the microbial content of the rumen of the ruminants, the process comprising the steps of:

mixing a lactic acid producing bacteria culture and a lactate utilizing bacteria culture;

admixing said bacteria cultures with an animal feedlot diet selected from the group consisting of corn, dried grain, alfalfa, corn meal, said admixing forming a composition; and, administering said composition orally to the ruminants, said lactic acid producing bacteria culture producing lactic acid in the rumen of the ruminant in order to promote the growth of said lactate utilizing bacteria culture in order to prepare the rumen for a feed diet which generates high levels of lactic acid in the rumen, said lactate utilizing bacteria culture consuming lactic acid produced in the rumen thereby decreasing levels of lactic acid in the rumen.

2. The process according to claim 1 wherein said lactic acid producing bacteria culture is selected from the group consisting of *Lactobacillus acidophilus, Lactobacillus plantarum, Streptococcuus faecium, Lactobacillus casei, lactobacillus lactis, Lactobacillus enterii, Lactobacillus fermentum, Lactobacillus delbruckii, Lactobacillus helveticus, Lactobacillus curvatus, Lactobacillus brevis, Lactobacillus bulgaricus, Lactobacillus cellobiosuus, Streptococcus lactis, Streptococcus thermophilus, Streptococcus cremoris, Streptococcus diacetylactis, Streptococcus intermedius, Bifidobacterium animalis, Bifidobacterium adolescentis, Bifidobacterium bifidum, Bifidobacterium infantis, Bifidobacterium longum, Bifidobacterium thermephilum, Pediococcus acidilactici,* and *Pediococcus pentosaceus.*

3. The process according to claim 1 wherein said lactic acid utilizing bacteria culture is selected from the group consisting of Propionibacterium, *Propionibacterium freudenreichii, Propionibacterium shermanii, Propionibacterium acidi-propionici, Propionibacterium globosum, Propionibacteriuum jensenii, Peptostreptococcus asaccharolyticus, Megasphaera elsdenii* and *Selenomonas ruminantium.*

4. The process according to claim 2 wherein said *Lactobacillus acidophilus* is the strain designated as *Lactobacillus acidophilus* ATCC 53545.

5. The process according to claim 3 wherein said Propionibacterium is the strain selected from the group consisting of Propionibacterium P-99 and Propionibacterium P-42.

6. The process according to claim 3 wherein said Propionibacterium is the strain designated as Propionibacterium P-5.

7. The process according to claim 3 wherein said composition is in a dry powder form for storage at ambient temperatures for long durations.

8. A process for improving the utilization of feedstuffs by ruminants through adjusting the microbial content of the rumen of the ruminants, the process comprising the step of:

mixing a culture of *Lactobacillus acidophilus* ATCC 53545, a culture of Propionibacterium P-5 and a culture of Propionibacterium P- 99;

admixing said cultures with an animal feedlot diet selected from the group consisting of corn, dried grain, alfalfa, corn meal, said aadmixing forming a composition; and, administering said composition orally to the ruminats, said culture of *Lactobacillus acidophilus* ATCC 53545 producing lactic acid in the rumen of the ruminant in order to promote the growth of said culture of Propionibacterium P-5 and said culture of Propionibacterium P-99 in order to prepare the rumen for a feed diet which generates high levels of lactic acid in the rumen, said culture of Propionibacterium P-5 and said culture of Propionibacterium P-99 consuming lactic acid produced in the rumen thereby decreasing levels of lactic acid in the rumen.

9. The process according to claim 8 wherein said composition is in a dry powder form for storage at ambient temperatures for long durations.

10. A process for improving the utilization of feedstuffs by ruminants through adjusting the microbial content of the rumen of the ruminants, the process comprising the steps of:

mixing a lactic acid producing bacteria culture and a lactate utilizing bacteria culture;

admixing said bacteria cultures with a dry formulation selected from the group consisting of growth substrates, enzymes, sugars, carbohydrates, extracts, and growth promoting micro ingredients, sid admixing forming a composition; and, administering said composition orally to the ruminants, said lactic acid producing bacteria culture producing lactic acid in the rumen of the ruminant in order to promote the growth of said lactate utilizing bacteria culture in order to prepare the rumen for a feed diet which generates high levels of lactic acid in the rumen, said lactate utilizing bacteria culture consuming lactic acid produced in the rumen thereby decreasing levels of lactic acid in the rumen.

11. The process according to claim 10 wherein said lactic acid producing bacteria culture is selected from the group consisting of *Lactobacillus acidophilus, Lactobacillus plantarum, Streptococcuus faecium, Lactobacillus casei, Lactobacillus lactis, Lactobacillus enterii, Lactobacillus fermentum, Lactobacillus delbruckii, Lactobacillus helveticus, Lactobacillus curvatus, Lactobacillus brevis, Lactobacillus bulgaricus, Lactobacillus cellobiosuus, Streptococcus lactis, Streptococcus thermophilus, Streptococcus cremoris, Streptococcus diacetylactis, Streptococcus intermedius, Bifidobacterium animalis, Bifidobacterium adolescentis, Bifidobacterium bifidum, Bifidobacterium infantis, Bifidobacterium longum, Bifidobacterium thermephilum, Pediococcus acidilactici,* and *Pediococcus pentosaceus.*

12. The process according to claim 10 wherein said lactic acid utilizing bacteria culture is selected from the group consisting of Propionibacterium, *Propionibacterium freudenreichii, Propionibacterium shermanii, Propionibacterium acidi-propionici, Propionibacterium globosum, Propionibacteriuum jensenii, Peptostreptococcus asaccharolyticus, Megasphaera elsdenii* and *Selenomonas ruminantium.*

13. The process according to claim 11 wherein said *Lactobacillus acidophilus* is the strain designated as *Lactobacillus acidophilus* ATCC 53545.

14. The process according to claim 12 wherein said Propionibacterium is the strain selected from the group consisting of Propionibacterium P- 99 and Propionibacterium P-42.

15. The process according to claim 12 wherein said Propionibacterium the strain designated as Propionibacterium P-5.

16. A process for improving the production of meat and milk from ruminants throughout a predetermined feeding period, through adjusting the microbial content of the rumen of the ruminants, the process comprising:

mixing a lactic acid producing bacteria culture and a lactate utilizing bacteria culture;

admixing said bacteria cultures with an animal feedlot diet selected from the group consisting of corn, dried grain, alfalfa, corn meal, said admixing forming a composition; and, administering said composition orally to the ruminants on a daily basis during the predetermined feeding period, said lactic acid producing bacteria culture producing lactic acid in the rumen of the ruminant in order to promote the growth of said lactate utilizing bacteria culture in order to prepare the rumen for a feed diet which generates high levels of lactic acid in the rumen, said lactate utilizing bacteria culture consuming lactic acid produced in the rumen thereby decreasing levels of lactic acid in the rumen.

17. The process according to claim 16 wherein said lactic acid producing bacteria culture is selected from the group consisting of *Lactobacillus acidophilus, Lactobacillus plantarum, Streptococcuus faecium, Lactobacillus casei, Lactobacillus lactis, Lactobacillus enterii, Lactobacillus fermentum, Lactobacillus delbruckii, Lactobacillus helveticus, Lactobacillus curvatus, Lactobacillus brevis, Lactobacillus bulgaricus, Lactobacillus cellobiosuus, Streptococcus lactis, Streptococcus thermophilus, Streptococcus cremoris, Streptococcus diacetylactis, Streptococcus intermedius, Bifidobacterium animalis, Bifidobacterium adolescentis, Bifidobacterium bifidum, Bifidobacterium infantis, Bifidobacterium longum, Bifidobacterium thermephilum, Pediococcus acidilactici,* and *Pediococcus pentosaceus.*

18. The process according to claim 16 wherein said lactic acid utilizing bacteria culture is selected from the group consisting of Propionibacterium, *Propionibacterium freudenreichii, Propionibacterium shermanii, Propionibacterium acidi-propionici, Propionibacterium globosum, Propionibacteriuum jensenii, Peptostreptococcus asaccharolyticus, Megasphaera elsdenii* and *Selenomonas ruminantium.*

19. The process according to claim 17 wherein said *Lactobacillus acidophilus* is the strain designated as *Lactobacillus acidophilus* ATCC 53545.

20. The process according to claim 18 wherein said Propionibacterium is the strain is selected from the group consisting of Propionibacterium P-99 and Propionibacterium P-42.

21. The process according to claim 18 wherein said Propionibacterium is the strain designated as Propionibacterium P-5.

22. The process according to claim 16 wherein said composition is in a dry powder form for storage at ambient temperatures for long durations.

23. A process for improving the transition of bovines from a roughage diet to a feedlot diet through adjusting the microbial content of the rumen of the bovine, the process comprising the steps of:
   mixing a culture of *Lactobacillus acidophilus* ATCC 53545, a culture of Propionibacterium P-5 and a culture of Propionibacterium P- 99;
   admixing said cultures with a dry formulation selected from the group consisting of growth substrates, enzymes, sugars, carbohydrates, extracts, and growth promoting micro ingredients, said admixing forming a composition; and,
   administering said composition orally to the bovines during the transition period, said culture of *Lactobacillus acidophilus* ATCC 53545 producing lactic acid in the rumen of the ruminant in order to promote the growth of said culture of Propionibacterium P-5 and said culture of Propionibacterium P-99 in order to prepare the rumen for a feed diet which generates high levels of lactic acid in the rumen, said culture of Propionibacterium P-5 and said culture of Propionibacterium P-99 consuming lactic acid produced in the rumen thereby decreasing levels of lactic acid in the rumen.

24. The process according to claim 23 wherein said composition is in a dry powder form for storage at ambient temperatures for long durations.

25. The process of claim 1, further comprising:
   producing microbial protein as a product of said lactic acid utilizing bacteria's consumption of lactic acid.

26. The process of claim 25, further comprising:
   increasing the production of microbial protein by increasing the production of lactic acid available for consumption by said lactic acid utilizing bacteria through the provision of said lactic acid producing bacteria.

27. A process for making a feed additive that improves the utilization of feedstuffs that generate high levels of lactic acid by a ruminant, said process comprising the steps of:
   providing lactic acid producing bacteria as a ruminant feed additive for increasing lactic acid levels in the rumen of an ingesting ruminant;
   providing lactic acid utilizing bacteria as a ruminant feed additive for decreasing lactic acid levels in the rumen of an ingesting ruminant; and
   promoting an increase in said lactic acid utilizing bacteria by the provision of said lactic acid producing bacteria.

28. The process of claim 27, further comprising:
   producing microbial protein as a product of said lactic acid utilizing bacteria's consumption of lactic acid.

29. The process of claim 28, further comprising:
   increasing the production of microbial protein by increasing the production of lactic acid available for consumption by said lactic acid utilizing bacteria through the provision of said lactic acid producing bacteria.

* * * * *